United States Patent
Simonetti et al.

(10) Patent No.: US 6,434,412 B1
(45) Date of Patent: Aug. 13, 2002

(54) CARDIAC CINE IMAGING WITH A SHORT REPETITION TIME AND HIGH CONTRAST BETWEEN THE BLOOD AND THE MYOCARDIUM

(75) Inventors: Orlando P. Simonetti; Jeffrey M. Bundy, both of Naperville; J. Paul Finn, Chicago, all of IL (US); Randall Kroeker, Winnipeg (CA)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

(21) Appl. No.: 09/316,650

(22) Filed: May 21, 1999

(51) Int. Cl.$^7$ ................................................ A61B 5/055
(52) U.S. Cl. ........................ 600/410; 600/413; 324/309
(58) Field of Search ................................ 600/410, 411, 600/413; 324/307, 309

(56) References Cited

U.S. PATENT DOCUMENTS

| | | | |
|---|---|---|---|
| 5,273,040 A | * 12/1993 | Apicella et al. ............ 600/410 |
| 5,337,000 A | * 8/1994 | Bruder .......................... 324/309 |
| 5,447,155 A | * 9/1995 | NessAiver et al. .......... 600/410 |
| 5,545,992 A | * 8/1996 | Foo .............................. 324/309 |
| 5,668,474 A | * 9/1997 | Heid ............................ 324/309 |
| 5,997,883 A | * 12/1999 | Epstein et al. ............... 324/309 |
| 6,034,528 A | * 3/2000 | Heid ............................ 324/309 |
| 6,073,041 A | * 6/2000 | Hu et al. ...................... 600/410 |
| 6,078,175 A | * 6/2000 | Foo .............................. 324/306 |

OTHER PUBLICATIONS

Westbrook et al., MRI in Practice, Blackwell Scientific Publications, 1993, pp. 102–131 and 200–203.*

Heid, O. "TrueFisp Cardiac Fluoroscopy" 1997, Abstract Proceedings of the ISMRM, p. 320.

* cited by examiner

Primary Examiner—Ruth S. Smith
(74) Attorney, Agent, or Firm—Mark H. Jay

(57) ABSTRACT

A segmented cine MR pulse sequence of the "TrueFISP"-type having a short repetition time TR is used to acquire MR data during a single breath hold. In the resulting cine images, the blood and the myocardium have distinctly different image contrasts.

10 Claims, 4 Drawing Sheets

Prospectively Gated Segmented TrueFISP Acquisition
A prescribed number of lines of MR data are acquired following R-wave trigger.
Then, RF pulses continue while data acquisition pauses and waits for next R-wave trigger.

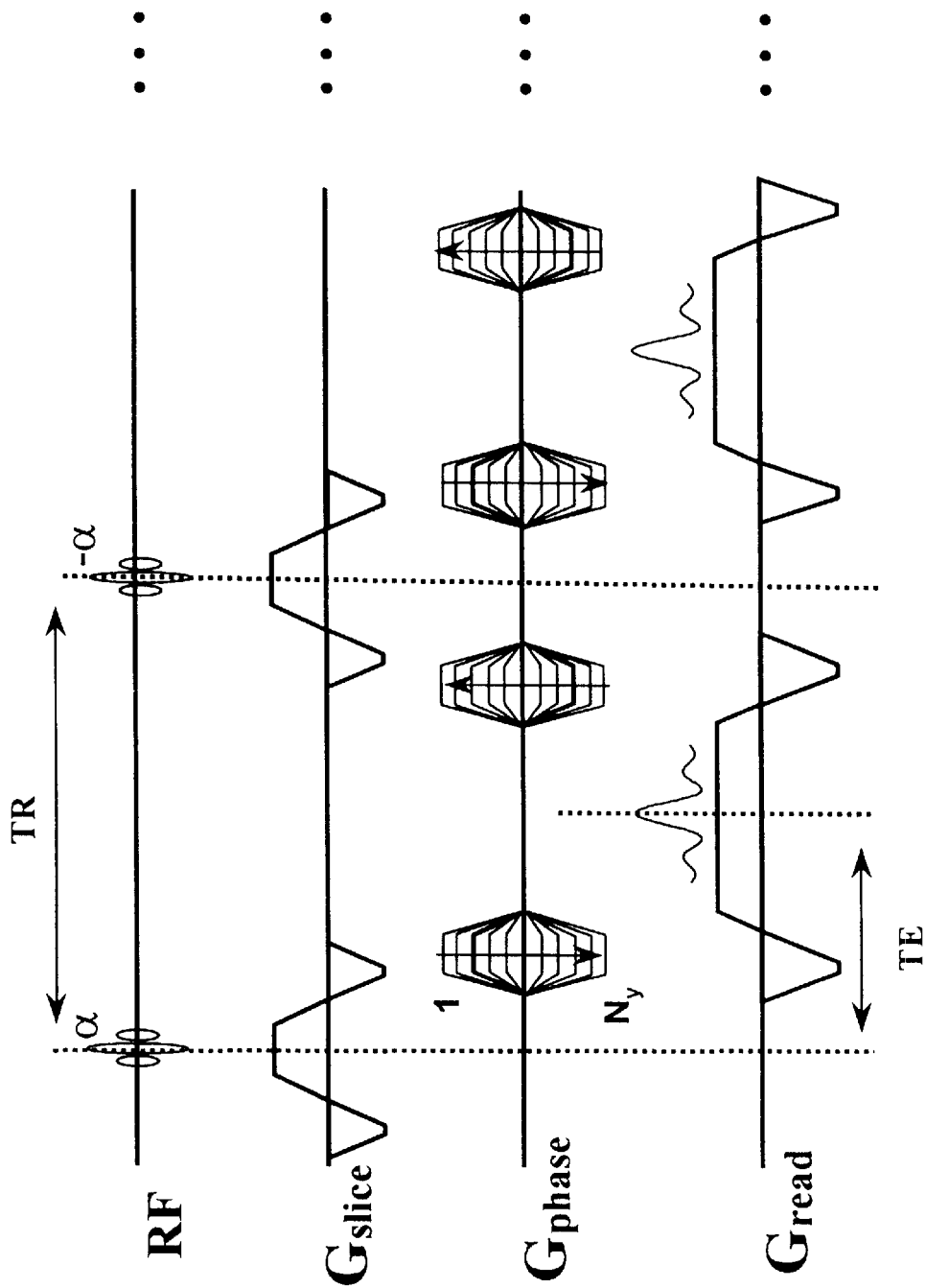
Fig. 1: 2D TrueFISP Pulse Sequence Timing Diagram

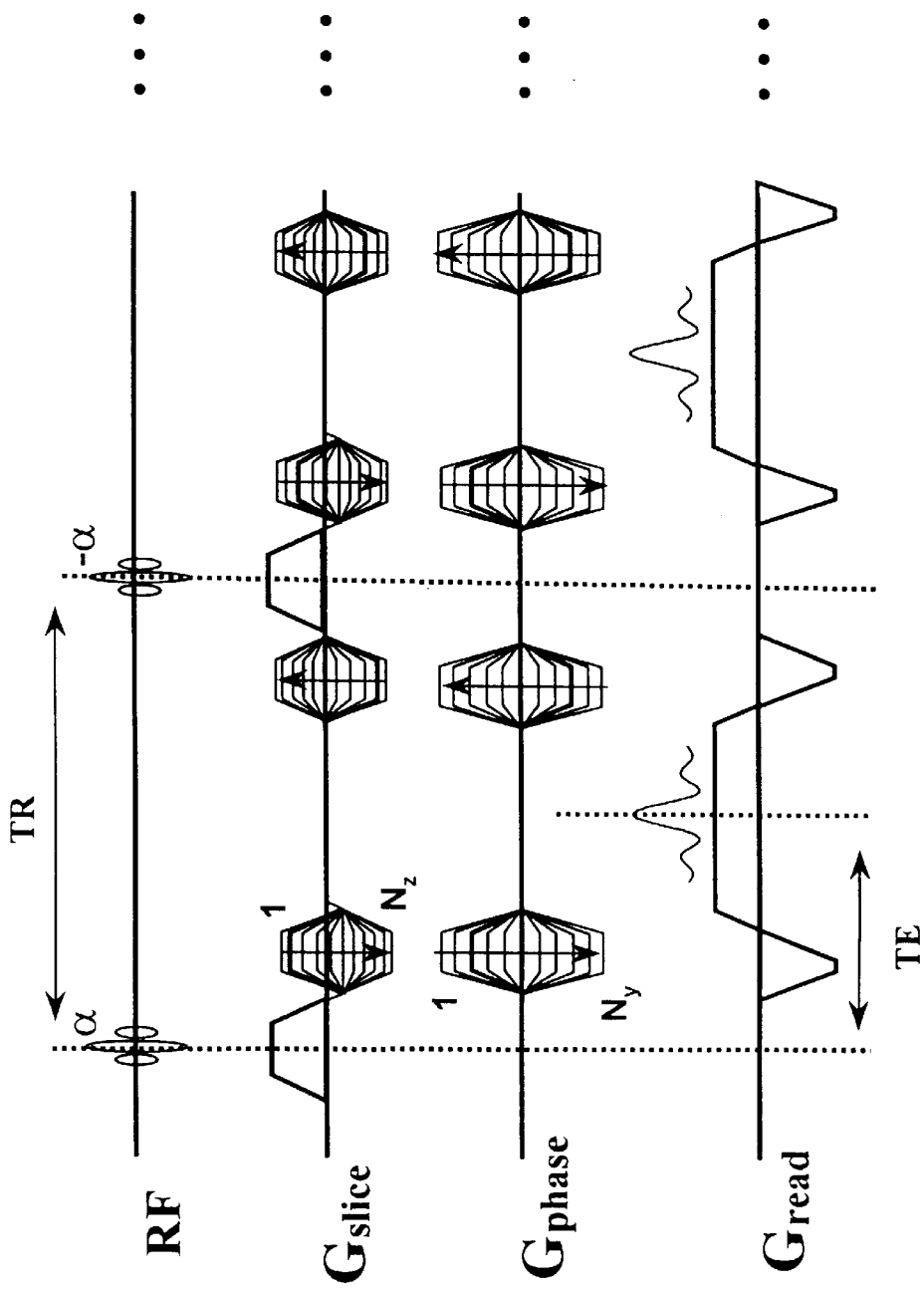
Fig. 2: 3D TrueFISP Pulse Sequence Timing Diagram

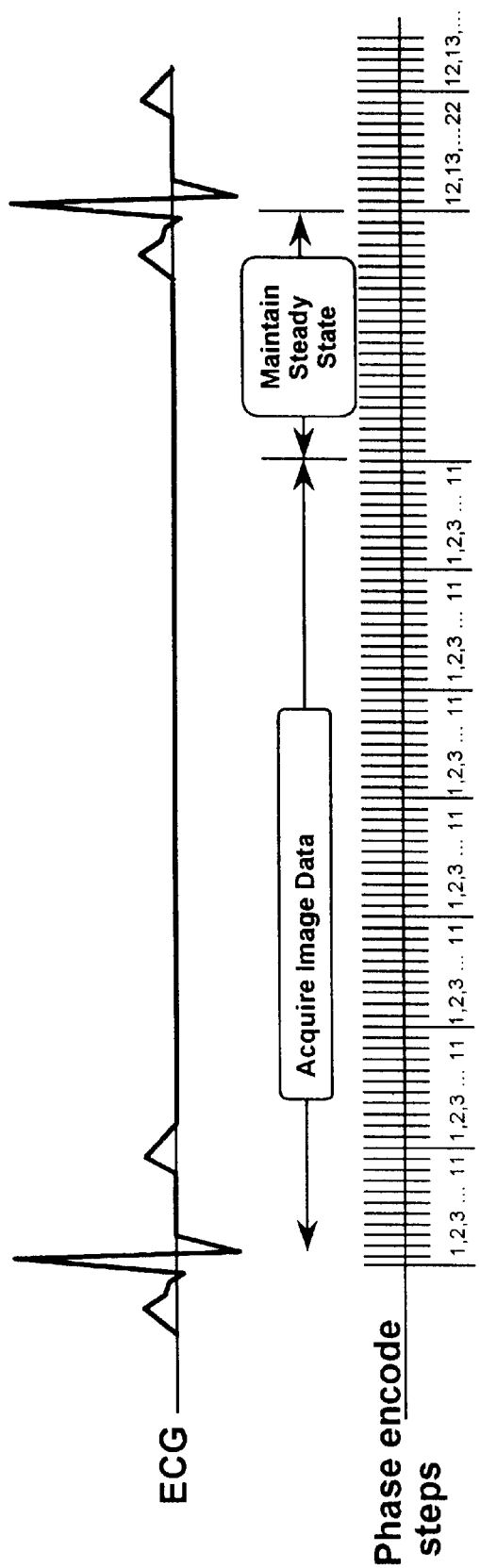
Fig. 3: Prospectively Gated Segmented TrueFISP Acquisition
A prescribed number of lines of MR data are acquired following R-wave trigger. Then, RF pulses continue while data acquisition pauses and waits for next R-wave trigger.

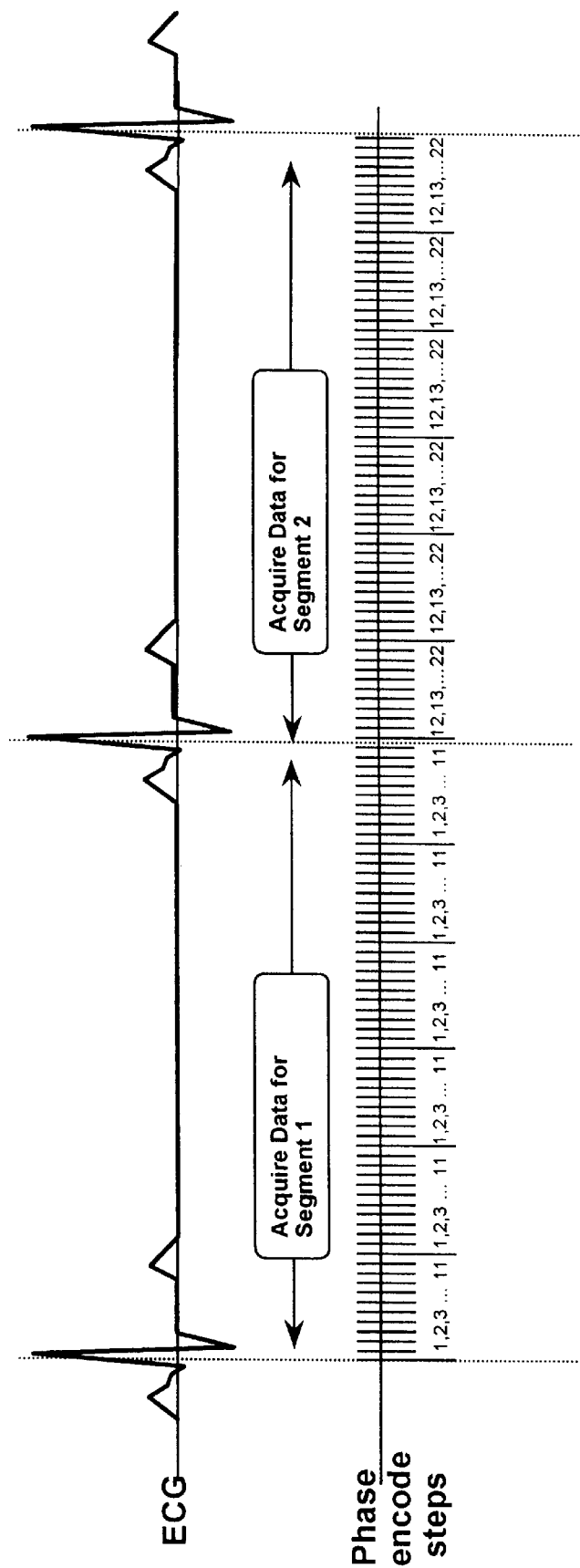
Fig. 4: Retrospectively Gated Segmented TrueFISP Acquisition
Continuous data acquisition. Time elapsed since previous R-wave is recorded for each line of data acquired. Lines are sorted retrospectively based on their position within the cardiac cycle.

CARDIAC CINE IMAGING WITH A SHORT REPETITION TIME AND HIGH CONTRAST BETWEEN THE BLOOD AND THE MYOCARDIUM

BACKGROUND OF THE INVENTION

The invention relates to MR imaging, and more particularly relates to MR imaging of the heart. In its most immediate sense, the invention relates to MR cine images of the heart such as are used to assess cardiac function and anatomy.

When cardiac function is to be evaluated using cine MR imaging, the image should distinguish clearly between the blood and the myocardium. Conventionally, this is accomplished by using a spoiled gradient-echo MR pulse sequence in which inflowing blood has a more intense signal than myocardium does.

Such a conventional technique can produce unsatisfactory results when the repetition time TR is decreased (as when a cardiac function study is to be carried out during a single breath hold). During a very short repetition time, only a small volume of blood can flow into a slice of interest. For this reason, when the repetition time is short so that one RF pulse follows quickly after another, only a small fraction of the blood within a slice of interest is replaced by inflowing blood. The blood that remains in the slice therefore becomes saturated, diminishing the difference between the signal intensity of the blood and the signal intensity of the myocardium. This problem is particularly acute in standard long-axis and four-chamber views of the heart. In these views, blood flow is primarily parallel to the slice plane, and little or no saturated blood is replaced between one RF pulse and the next RF pulse.

At short repetition times, certain MR pulse sequences (e.g. sequences referred to as "TrueFISP" sequences) produce image contrast as a function of the T2/T1 ratio (rather than relying upon blood flow for contrast). Such MR pulse sequences would therefore be appropriate candidates for use in cardiac function studies (since the T2/T1 ratio of blood significantly exceeds the T2/T1 ratio of the myocardium).

Accordingly, it would be advantageous to provide a method for conducting a cardiac imaging MR study, and particularly a cardiac functional MR study, in which the contrast between the blood and the myocardium remained significant at short repetition times TR, whereby the study could be conducted during a shorter breath hold (or, alternatively, conducted with higher temporal or spatial resolution than using MR sequences in which the repetition time TR is longer).

The invention proceeds from the realization that when a TrueFISP-type of MR pulse sequence is used to image the heart and the blood therein, segmenting the MR pulse sequence not only reduces (and possibly eliminates) artifacts caused by respiratory motion but also reduces the acquisition time so that the acquisition can be completed within a reasonable breath-hold (on the order of ten to twenty heartbeats). This makes it possible to produce MR cine images having adequate spatial and temporal resolution in a relatively short period of time.

As used in this patent application and as understood by persons skilled in the art, a "segmented" MR pulse sequence is one that causes the final k-space matrix to be built up from sub-matrices comprising groups of lines of MR data, the lines in each group being distributed over more than one cardiac cycle. To understand the meaning of this term, two examples of unsegmented MR pulse sequences will be compared with a segmented MR pulse sequence.

In the first instance, let it be assumed that a particular k-space matrix is made up of 165 lines of MR data taken at different phase-encodings and that a typical unsegmented MR pulse sequence is used to acquire the MR data. In this instance, one line of data would typically be acquired during each cardiac cycle, so that 165 heartbeats would be required to complete the image acquisition. Few if any patients could hold their breath for such a long time. The result would be an MR acquisition having a very long duration and producing a reconstructed image having a very high temporal resolution.

In a second instance, let it be assumed that all 165 lines of MR data were to be acquired during a single cardiac cycle (i.e. during a single heartbeat), using an unsegmented MR pulse sequence. In this instance, the time needed to acquire each image would be too long to accurately depict cardiac function, even if the repetition time TR were chosen to be very short. In this instance, the MR acquisition would have a very short duration and would produce a reconstructed image having a very low temporal resolution.

In the third and last instance, let it be assumed that a segmented MR pulse sequence were to be used to acquire the 165 lines of MR data. In this instance, some (e.g. eleven) lines of MR data would be acquired during one heartbeat and the rest acquired during other heartbeats (i.e. eleven per heartbeat during fourteen more heartbeats so that a total of 165 lines of MR data would ba acquired over fifteen heartbeats). This MR acquisition would have a moderate duration and would produce a reconstructed image having a moderate temporal resolution.

In accordance with the invention, a segmented but otherwise conventional TrueFISP-type cine MR pulse sequence is used to image the patient's heart and the blood therein. (Advantageously but not necessarily, this is done during a single breath-hold.) Initially, the magnetizations of the heart and blood are brought to a steady-state. Then, lines of MR data are acquired using the segmented TrueFISP-type MR pulse sequence. (During this data acquisition, the magnetizations of the heart and blood remain in steady-state, because this is an intrinsic characteristic of TrueFISP-type MR pulse sequences.)

The MR pulse sequence may be of the two-dimensional type or of the three-dimensional type. In one preferred embodiment, MR data acquisition is gated to the patient's cardiac cycle. In accordance with this embodiment, the steady-state magnetizations of the heart and blood are maintained regardless whether lines of MR data are being acquired. In another preferred embodiment, MR data acquisition continues without interruption while the patient's cardiac cycle is monitored, and the data are retrospectively gated to form multiple images, each representing the state of the heart at a different time within a composite cardiac cycle.

BRIEF DESCRIPTION OF THE DRAWINGS

The invention will be better understood with the aid of the illustrative and non-limiting drawings, in which:

FIG. 1 shows a two-dimensional MR pulse sequence of the TrueFISP type;

FIG. 2 shows a three-dimensional MR pulse sequence of the TrueFISP type;

FIG. 3 is a timing diagram schematically illustrating a first preferred embodiment of the invention; and FIG. 4 is a timing diagram schematically illustrating a second preferred embodiment of the invention.

DETAILED DESCRIPTION OF PREFERRED EMBODIMENTS

Referring first to FIG. 1, it can be seen that in a two-dimensional TrueFISP-type MR pulse sequence, the time integrals of the slice-select gradient, the phase-encoding gradient, and the read gradient are all zero at the center of each RF pulse. The same is true for a three-dimensional TrueFISP MR pulse sequence (FIG. 2). As a result, the magnetization of the sample remains in a steady-state while lines of MR data are being acquired.

Turning now to the first preferred embodiment as schematically illustrated in FIG. 3, the magnetizations of the heart and blood contained therein are initially brought to steady-state by applying the same RF pulses that are later used during acquisition of MR data. The patient's cardiac cycle is monitored and used to gate data acquisition prospectively; acquisition of lines of MR data commences when an R-wave is detected. Then, lines of MR data are acquired over e.g. 15 cardiac cycles. If for example each k-space matrix is chosen to have 165 lines, eleven lines (a "segment") might be acquired during each cardiac cycle so that each k-space matrix is filled after 15 cardiac cycles. In one possible implementation, lines 1, 16, 31, 46, 61, 76, 91, 106, 121, 136, 151 might be acquired during the first cardiac cycle. Then, lines 2, 17, 32, 47, 62, 76, 91, 107, 122, 136, 152 might be acquired during the second cardiac cycle. Lines 3, 18, 33, 48, 63, 77, 92, 108, 123, 136, 153 might be acquired during the third cardiac cycle, and this process would be continued until all 165 lines of MR data had been acquired to fill up the full k-space matrix for each image in the cine series. (The order in which the lines of MR data are acquired need not be as stated. For example, it would also be possible to acquire lines 1–11 during the first cardiac cycle, lines 12–22 during the second cardiac cycle, and lines 23–33 during the third cardiac cycle, and so on. The order in which the lines of MR data are acquired is not part of the invention.)

If it is assumed that 220 lines of MR data are acquired during each cardiac cycle, then at the end of a single breath hold sufficient data will have been acquired to fill up twenty 165-line k-space matrices. Accordingly, twenty MR images can be reconstructed to form a 20-image cine loop, and the image loop displayed. Echo-sharing and other data interpolation techniques can be used to arbitrarily increase the number of reconstructed images.

In this first preferred embodiment, acquisition of lines of MR data will likely occur during only a fraction of each cardiac cycle. Hence, there will be a period between the end of MR data acquisition in a current cardiac cycle and the beginning of MR data acquisition in the next cardiac cycle. During this period, RF pulses must be continued, to keep the magnetizations of the heart and blood in steady-state. If these pulses are not continued, the magnetizations of the heart and the blood will die out and will not be in steady-state at the beginning of the next cardiac cycle, when MR data acquisition begins once again.

In accordance with the second preferred embodiment of the invention as is schematically illustrated in FIG. 4, lines of MR data are acquired continuously during a single breath hold while the patient's cardiac cycle is monitored. Then, the acquired MR data are retrospectively gated, reconstructed into cine MR images, and displayed.

A segmented TrueFISP MR pulse sequence was implemented on a 1.5T Magnetom Sonata (Siemens Medical Systems, Iselin N.J.) with a high performance gradient system (40 mT/m amplitude, 200 T/m/sec slew rate). Echo-sharing was used to improve temporal resolution. The basic TrueFISP timing module used has TR=4.0 ms and TE=2.0 ms. Segmented TrueFISP pulse sequences with various numbers of lines per segment have been implemented. Typical imaging parameters for an 11 line/segment segmented TrueFISP sequence are 165×256 pixels with dimensions of 1.5 mm×1.25 mm×6 mm slice thickness acquired over 15 heartbeats. The flip angle ($\alpha$) is set to the maximum allowed by SAR (Specific Absorption Rate) limitations in each patient; it is typically in the range of 50° to 70°. The receiver bandwidth (sampling rate) was 780 Hz/pixel. A CP 4-channel phased array body coil was used. The above example is merely exemplary, and the various parameters can and should be varied in accordance with the patient's condition and the intended use for the results of the MR study.

Although one or more preferred embodiments have been described above, the scope of the invention is defined only by the following claims:

1. A method of conducting a cardiac imaging study on a living patient using magnetic resonance (MR) imaging comprising the following steps:

preparing the patient's heart and the blood contained therein with a series of RF pulses having an alternating phase while acquiring no lines of MR data, whereby the magnetizations of the heart and the blood are brought to steady-state before MR image data are acquired;

acquiring cine MR image data of the heart and blood contained therein in successive cardiac cycles, using a segmented gradient-echo MR pulse sequence having short repetition time TR, the MR pulse sequence including a phase-encoding gradient, a slice-select gradient, and a read gradient wherein RF phase is alternated and gradient rewinding is used on the phase-encoding gradient, the slice-select gradient, and the read gradient, in such a manner that the time integral of each gradient is zero at the center of each RE pulse to maintain the magnetization of the heart and blood in steady-state; and maintaining the magnetization in the steady state between said successive cardiac cycles.

2. The method of claim 1, wherein the MR pulse sequence is of a two-dimensional type.

3. The method of claim 1, wherein the MR pulse sequence is of a three-dimensional type.

4. The method of claim 1, wherein said acquiring step is gated to the patient's cardiac cycle and said magnetization of the heart is maintained in steady-state after one acquisition and before the next acquisition.

5. The method of claim 4, wherein said acquiring step is carried out during a single breath-hold.

6. The method of claim 1, wherein the acquisition step is carried out uninterruptedly while monitoring the patient's cardiac cycle, and further comprising the step of retrospectively gating the acquired cine MR data.

7. The method of claim 6, wherein the acquiring step is carried out during a single breath-hold.

8. The method of claim 1 wherein the pulse sequence is a TrueFISP-type pulse sequence.

9. A method of conducting a cardiac imaging study on a living patient using magnetic resonance (MR) imaging, comprising the following steps:

preparing the patient's heart and the blood contained therein with a series of RF pulses having an alternating phase while acquiring no lines of MR data, whereby the magnetization of the heart and the blood are brought to steady-state before MR image data are acquired;

acquiring cine MR image data of the heart and blood contained therein in successive cardiac cycles, using a segmented gradient-echo MR pulse sequence including a phase-encoding gradient, a slice-select gradient, and a read gradient wherein RF phase is alternated and gradient rewinding is used on the phase-encoding gradient, the slice-select gradient, and the read gradient, in such a manner that the time integral of each gradient is zero at the center of each RF pulse to maintain the magnetization of the heart and blood in steady-state;

maintaining the magnetization in the steady state between said successive cardiac cycles; and reconstructing, from said acquired cine MR image data, a cine image of patient's heart; and displaying the reconstructed image.

10. The method of claim 9 wherein the pulse sequence is a TrueFISP-type pulse sequence.

* * * * *